United States Patent
Abdulwahed et al.

(10) Patent No.: US 7,094,942 B2
(45) Date of Patent: Aug. 22, 2006

(54) CARBON DIOXIDE PROMOTED DEHYDROGENATION PROCESS FOR OLEFINS

(75) Inventors: Mazhar Abdulwahed, Damascus (SY); Leal G. Canelon, Riyadh (SA); Adel Alshafai, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 529 days.

(21) Appl. No.: 10/383,784

(22) Filed: Mar. 7, 2003

(65) Prior Publication Data

US 2004/0181107 A1    Sep. 16, 2004

(51) Int. Cl.
C07C 5/333    (2006.01)
C07C 5/373    (2006.01)

(52) U.S. Cl. ..................... 585/662; 585/658
(58) Field of Classification Search ................ 585/658, 585/652, 662
See application file for complete search history.

(56) References Cited

U.S. PATENT DOCUMENTS

| | | | | |
|---|---|---|---|---|
| 3,180,903 A | * | 4/1965 | Harnsberger et al. | 585/630 |
| 3,505,422 A | * | 4/1970 | Killian et al. | 585/445 |
| 3,697,614 A | | 10/1972 | Tomezski | 585/658 |
| 3,725,249 A | | 4/1973 | Vesely | 208/139 |
| 4,046,833 A | | 9/1977 | Hardman | 585/658 |
| 4,788,371 A | | 11/1988 | Imai et al. | 585/443 |
| 4,996,387 A | | 2/1991 | Gerhold et al. | 585/654 |

* cited by examiner

Primary Examiner—Walter D. Griffin
Assistant Examiner—In Suk Bullock
(74) Attorney, Agent, or Firm—Kramer Levin Naftalis & Frankel LLP

(57) ABSTRACT

A process for the dehydrogenation of alkane hydrocarbons is disclosed. The process comprises contacting the alkane with a chromium-based dehydrogenation catalyst in the presence of carbon dioxide at a temperature of from about 400° C. to about 700° C., a pressure of from about 0.1 to about 10 atmospheres, wherein the alkane to carbon dioxide molar ratio is about 1:0.0001 to 1:0.045.

14 Claims, 8 Drawing Sheets

FIG. 4
Coke Selectivity v. Carbon Dioxide Concentration

FIG. 8
Coke Selectivity v. Carbon Dioxide Concentration

CARBON DIOXIDE PROMOTED DEHYDROGENATION PROCESS FOR OLEFINS

FIELD OF THE INVENTION

This invention relates to a process for the production of olefins (alkenes) by the normal dehydrogenation of a corresponding paraffin (alkane). More particularly, this invention relates to an improved dehydrogenation process for olefin production employing chromium-based dehydrogenation catalysts in the presence of carbon dioxide.

BACKGROUND INFORMATION

The dehydrogenation of hydrocarbons is an important commercial process. This is because of the great demand for dehydrogenated hydrocarbons as feedstocks for industrial processes. For example, dehydrogenated hydrocarbons are utilized in the manufacture of detergents, high octane gasolines, pharmaceutical products, plastics and synthetic rubbers, and various other products. One example of a specific dehydrogenation process is dehydrogenating isobutane to produce isobutylene, which may then be polymerized to provide tackifying agents for adhesives, viscosity-index additives for motor oils and impact-resistant and anti-oxidant additives for plastics. Isobutylene may also used in the manufacture of Methyl Tertiary Butyl Ether (MTBE) or may be dimerized to isooctane. MTBE and isooctane are used as anti-knocking agents in gasoline fuels.

The major traditional sources of alkenes have been steam cracking, and fluid catalytic cracking. Both processes simultaneously provide a wide range of other products with limited flexibility. However, as the demand grows for specific alkenes, such as isobutylene or propylene, it is not cost effective to satisfy that demand utilizing expensive cracking units. The best technical choice for providing alkenes has been the normal dehydrogenation of alkanes.

Major factors affecting the technical implementation of alkane dehydrogenation are (1) the thermodynamic equilibrium limiting single pass conversion as well as (2) the endothermic character of the dehydrogenation reaction. Additionally, the temperature required to carry out conventional dehydrogenation causes thermal cracking which lowers alkene selectivity, especially in the case of propane dehydrogenation.

Two types of catalysts based on chromium oxides for the dehydrogenation of lower alkanes have been described in the scientific and patent literature: chromium oxides supported on $\gamma,\delta/,\theta$-alumina doped with alkali metal, and chromium oxides supported on $ZrO_2$. Chromium oxides supported on $\gamma,\delta/,\theta$-alumina doped with alkali metal are employed in the Lumnus Catofin and Snamprogetti-Yarsintez fluidized bed dehydrogenation processes. As well, chromium oxides supported on $ZrO_2$ have been investigated for their higher thermal stability relative to alumina.

The precise nature of the active sites in chromium oxide-supported catalysts has been the subject of scientific debate for many years. As is known, $Cr_2O_3$ is the most stable form of all of the possible chromium oxides.

Two types of $Cr^{6+}$ species have been detected in chromium oxide supported on alumina, after the calcination treatment and before reaction. It is generally believed that after reduction with hydrogen, all $Cr^{6+}$ is reduced to $Cr^{3+}$. However, according to Grunert et al. (J. Catal. 110 (1986), 138), the reduction occurs in two steps: an initial very rapid step from $Cr^{6+}$ to $Cr^{3+}$, followed by a slower step from $Cr^{3+}$ to lower oxidation states ($Cr^{2+}$). The active sites of the dehydrogenation reactions have been assumed to be $Cr^{3+}$ by Grunert W. et al. (J. Catal. 99 (1986), 149; Delmon B. et al., J. Catal. 24 (1972), 336) Konig P. et al. (Acta Chim. Acad. Sci. Hung. 76 (1976), 123), both $Cr^{2+}$ and $Cr^{3+}$ by Ashmawy F. M. (J. Chem. Soc., Faraday Trans. 76 (1980), 2096), or coordinatively unsaturated $Cr^{2+}$ by Lunsford H. et al. (J. Catal. 91 (1985), 155).

The catalytic activity in the dehydrogenation of isobutane as well as of ethane has been found to be proportional to the chromium content, whichever the species present. Also, in the case of propane dehydrogenation over $ZrO_2$ supported chromium oxide (Indovina et al., Appl. Catal. 81 (1992), 113), the activity per atom of chromium was found to be the same for all chromium loadings. Such activity was attributed to the presence of mononuclear $Cr^{3+}$ species.

However, since hydrogen is present as part of the dehydrogenation reaction product, further reduction of $Cr^{3+}$ will continue. It is shown in this invention that the lower oxidation state chromium species are responsible for undesired cracking reactions taking place during dehydrogenation and thus to be responsible for coke formation. To minimize the formation of cracking products and coke, the oxidation state of chromium catalytic sites must be controlled by means of a functional redox system during the reaction cycle. Such a redox system according to the present invention is believed to be $Cr^{2+}/Cr^{3+}/CO_2$, as is demonstrated hereinbelow by the addition of carbon dioxide to the hydrocarbon in the feedstock.

It is known from the literature that oxygen can shift the thermodynamic equilibrium of dehydrogenation reactions towards increased olefin production by reacting with the hydrogen product. Oxygen is also believed to combust coke and thereby keep the catalyst surface clean of coke deposits. Regeneration of the catalyst is thereby avoided, since coke does not build up and consequently the catalyst is not deactivated. Such reactions are called oxidative dehydrogenation reactions. Up to date there is no commercial process available for producing light alkanes, especially $C_3$ and $C_4$-olefins, by oxidative dehydrogenation reactions due to the absence of a proper catalyst. Known oxidative dehydrogenation reaction processes are described in several published patents.

For example, U.S. Pat. No. 4,996,387 disclosed a dehydrogenation process with a continuous regeneration of dehydrogenation catalyst achieved by cyclically contacting a portion of the catalyst with an admixture of oxygen containing regeneration gas and diluent, while contacting the remaining portion of the catalyst with an admixture of hydrocarbon feed material and diluent. In this disclosure oxygen is added for the purpose of catalyst regeneration in a separate regime from the dehydrogenation medium.

Canadian Patent 912,051 describes a vapor phase process for dehydrogenation of paraffin and olefins with oxygen and halogen in the presence of a solid catalyst containing an alkali metal or an alkaline earth metal compound and a promoter. U.S. Pat. No. 3,697,614 is directed to olefin production by oxidative dehydrogenation using a molten alkali metal hydroxide containing alumina with an in solution transition metal oxygenation, preferably consisting of dichromate molybdate, tungstate, manganate, permanganate, ferrate and metavanadate.

U.S. Pat. No. 4,046,833 disclosed a vapor phase process for dehydrogenation of paraffinic hydrocarbon containing 3 to 6 carbon atoms to the corresponding monoolefin, wherein the process is carried out in the presence of oxygen and in the presence of an oxidative dehydrogenation catalyst containing vanadium and aluminum. The effective paraffin to oxygen ratio is claimed to be in the range of 1:0.04 to 1:10. Examples given in the disclosure demonstrate only the effect of several catalyst compositions tested under different conditions with different oxygen concentrations.

U.S. Pat. No. 4,788,371 discloses another oxidative dehydrogenation process using a dehydrogenation catalyst comprising at least one noble metal component. According to the disclosure, an alkane feed including an oxygen containing gas is introduced into a dehydrogenation reactor containing the noble metal catalyst. The oxygen added to the reactor feed is in a molar ratio to alkane which is very similar to that of U.S. Pat. No. 4,046,833. The effect of oxygen on the described system is to combust hydrogen while minimizing the combustion of valuable hydrocarbons.

Numerous processes have also been disclosed which involve the removal of hydrogen from a mixture of hydrogen and one or more organic compound. For example, U.S. Pat. No. 4,788,371, and other patents referenced therein, disclose a process for the dehydrogenation of hydrocarbons in which hydrogen obtained by the dehydrogenation of the hydrocarbons is catalytically reacted with oxygen. A disadvantage of each of these processes is that some of the oxygen gas reacts chemically with the organic compounds instead of the hydrogen, thus converting them into undesired products.

European Patents A1-0219271 and A1-0219272 also disclose processes for the dehydrogenation of hydrocarbons in which hydrogen obtained from such dehydrogenation is removed. In these processes, the dehydrogenation takes place in the presence of a zeolite catalyst, and the hydrogen is removed by chemical reaction with an acidic oxide such as sulfur dioxide or nitrous oxide. The processes do not share the disadvantage of processes which utilize oxygen gas because sulfur dioxide and nitrous oxide are not as reactive as is oxygen towards the organic compounds. They also appear to be less effective in the removal of hydrogen.

The oxidative dehydrogenation reaction processes described above have certain drawbacks. They generally suffer low olefin selectivity and currently are not utilized in commercial scale due to the lack of a suitably active and selective catalyst. A further disadvantage of all of these processes is the fact that using oxygen as a promoter of dehydrogenation reactions requires special handling. Oxygen can form explosive mixtures with hydrocarbons, and thus expensive explosion protection apparatus is generally required to safely utilize it on a commercial scale.

In the production of olefins by the catalytic dehydrogenation of paraffins, it is of course desirable to obtain as a high yield of olefin as possible in a single conversion pass. To minimize hot spot effects, and consequently increase the life of the catalyst, it is also desirable to conduct the reaction under such conditions wherein a minimum amount of coke is formed on the catalyst. It is also desired to increase the dehydrogenation reaction period by decreasing coke formation. Finally, it is desired to accomplish these goals using a "friendly" and safe nonexplosive reaction promoter, whose use does not require any investment in special safety equipment.

SUMMARY OF THE INVENTION

It is an object of the invention to provide a dehydrogenation process for the production of olefins which provides high alkane conversion and increased olefin selectivity.

It is another object of the invention to provide a process for hydrocarbon dehydrogenation for the production of olefins with high yield, less feedstock consumption and less coke formation.

It is another object of the present invention to extend dehydrogenation reaction cycle time.

It is another object of the invention to accomplish the above stated goals utilizing a nonexplosive promoter which can be safely used without expensive protection equipment.

Other objects and advantages of the invention will be apparent from the following description.

The present invention provides an improved process for the production of olefin by normal dehydrogenation of corresponding alkane, and especially for the improved dehydrogenation of hydrocarbons on chromium-based dehydrogenation catalysts using carbon dioxide. The chromium-based dehydrogenation catalyst useful in the instant process has been found to be surprisingly selective towards olefins in the presence of small amounts of carbon dioxide, resulting in an increase in the yield of the desired dehydrogenated product. Accordingly, the process of the present invention is broadly directed to a hydrocarbon conversion process, and specifically towards a process of dehydrogenation of hydrocarbons on chromium-based dehydrogenation catalysts using small amounts of carbon dioxide.

The hydrocarbon dehydrogenation process of the invention utilizes a dehydrogenation catalyst comprising 10–20% by weight of chromium to promote dehydrogenation of a feedstock comprising dehydrogenatable hydrocarbon and a small amount of pure carbon dioxide, wherein the hydrocarbon to carbon dioxide molar ratio should be between 1:0.0001 and 1:0.045. According to an exemplary preferred embodiment of the invention, the dehydrogenatable hydrocarbon is isobutane, the carbon dioxide is provided in an amount between 0.0001 to 0.001 gram mole carbon dioxide per gram chromium in the catalyst and reaction temperature being between 520° C. to 700° C.

In a further embodiment of the present invention, air or carbon dioxide containing gas is used in place of pure carbon dioxide.

DETAILED DESCRIPTION OF THE INVENTION

The present invention relates to an improved process for the production of olefins, and particularly isobutylene, by normal dehydrogenation of the corresponding paraffins. The process is aimed at minimizing the side reactions occurring during the dehydrogenation reaction by controlling the oxidation state of chromium sites in the dehydrogenation catalyst. This is achieved by the addition of small amounts of carbon dioxide. The addition of carbon dioxide according to the present invention provides an in situ heat source for the reaction, decreases coke formation, enhances olefin selectivity and extends the dehydrogenation catalytic cycle. In another embodiment of the invention, a carbon dioxide containing gas may be used in place of pure carbon dioxide.

The advantage of the present invention is maintaining high paraffin conversion while increasing olefin yield and selectivity, reducing thermal cracking, decreasing feedstock consumption and extending catalyst life.

The dehydrogenation catalysts useful in this invention comprise 10–20% by weight of chromium, and preferably, 12–18% by weight of chromium. The chromium-based dehydrogenation catalyst may be spray dried, pelletized or shaped, preferably it is spray dried. Exemplary catalysts that may be used in exemplary embodiments of the invention are the T-2715 catalyst, having approximately 14% chromium content, and available from United Catalyst, Inc. (now Sud Chemie, of Munich, Germany) or the Catofin standard chromia-amumina commercial catalyst from United Catalyst, Inc. (as above, now Sud Chemie) with a 12% chromium content, a surface area of 80–95 $m^2/gm$, a bulk density of 1.49–1.55 kg/liter and an average pellet diameter of 3 mm. Catalysts of equivalent or similar functionality may be used in other embodiments of the invention. The catalyst used in the instant process may be used alone, or supported on or impregnated in a carrier material. Suitable carrier materials include alumina, silica, thoria, zirconia, titania, boron phosphate, silicon carbide, pumice, diatomaceous earth, clay, and the like. The catalysts of the invention are preferably calcined to produce desirable physical properties such as attrition resistance, optimum surface area and particle size.

The dehydrogenation of a dehydrogenatable paraffinic hydrocarbon, such as isobutane, is effected in the instant process by contacting the dehydrogenatable paraffinic hydrocarbon, with the previously described catalyst at conditions suitable for normal dehydrogenation. Such conditions comprise temperatures which range from about 400° C. to about 700° C., preferably, between about 520° C. to about 700° C., and, more preferably, between about 540° C. to about 640° C., and a reaction pressure in the range of from about 0.1 to about 10 atmospheres.

Carbon dioxide concentration in the process of the present invention is critical to obtain the described benefits of the invention. In one exemplary embodiment, a required carbon dioxide amount for isobutane dehydrogenation is between 0.0001 to 0.001 gram mole carbon dioxide per gram chromium in the catalyst, preferably, between 0.0002 to 0 0008 gram mole carbon dioxide per gram chromium in the catalyst. In addition, the molar ratio of dehydrogenatable hydrocarbon to carbon dioxide is desirably between 1:0.0001 to 1:0.045, preferably, between 1:0.0005 to 1:0.04, more preferably, between 1:0.001 to 1:0.04, and most preferably between 1:0.01 to 1:0.04.

Carbon dioxide may be added to the instant process in various ways, such as, for example, by admixing carbon dioxide with a relatively cool alkane hydrocarbon feed stream or with a steam diluent, or it may be added directly to the reactor independently of the feed alkane hydrocarbons.

Inert diluent may be employed in the dehydrogenation process of this invention. Any inert material, which will not adversely affect the dehydrogenation process, may be employed as diluent. Examples of suitable diluents are methane, ethane, propane, nitrogen, or steam.

The process of the invention can be applied to any dehydrogenatable paraffinic hydrocarbon and in any type of dehydrogenation reactor, including fixed bed, moving bed and fluidized bed. Preferred embodiments of the invention utilized a fixed bed catalytic system or a dense phase moving bed system, such as is shown in U.S. Pat. No. 3,725,249.

One exemplary fixed bed catalytic reaction system embodiment of the present invention is comprised of a single reaction zone within a single reactor with single inlet to the reactor and with the products and by-products of the process exiting through a reactor outlet port.

In another exemplary embodiment of the invention, a fixed bed catalyst system has multiple carbon dioxide inlet ports separated along the reaction zone so that carbon dioxide can be injected at different points into the catalyst bed of the reaction zone. This type of configuration mimics a reaction system with a plurality of catalyst beds.

In an alternative exemplary embodiment, the process of the instant invention is accomplished in a moving bed catalytic system, such as, for example, the system described in U.S. Pat. No. 3,725,249. This example embodiment of the invention is most useful in the context of reactions where the catalyst is known to be deactivated by coke deposition thereon. In this example embodiment, the catalyst of the instant process continuously moves through the plurality of reaction zones of the process and, once deactivated, is transported to a continuous catalyst regeneration system. Once regenerated, the catalyst is returned to the reaction system.

EXAMPLES

The invention will now be more fully described and understood with reference to Examples 1 through 10. These examples are given by way of illustration and the claimed invention is not limited by these examples.

The following Examples 1–4 demonstrate the function of $CO_2$ vs. $O_2$ and methane addition as gaseous promoters. $CO_2$ is normally considered as a mild oxidant, whereas $CH_4$ has no oxidation properties. In Examples 1–4 the following procedure was utilized. The catalyst was a commercially available chromium-alumina based dehydrogenation catalyst containing 14% chromium and manufactured by spray dryer method (catalyst T-2715 from United Catalyst, Inc.).

Five or one grams of the catalyst were loaded in a standard SS fixed bed reactor constructed of a 1-inch tube. A ⅛ inch thermowell was located axially in the reactor tube to enable temperature measurement. The reactor was placed in an oven heated electrically for maintaining the desired temperature. The reactor effluent was directed to an on-line connected GC HP 6890 provided with FID and TCD detectors. Nitrogen was introduced into the reactor effluent at constant rate to provide an internal standard for accurately calculating the mass balance. The catalyst was pre-treated with 33.3 cc/min helium at the reaction temperature for five (5) minutes before introduction of the feed at the given composition into the reactor. Analysis of the reactor products were taken and reported in Tables A. After analysis of the reaction product, the reaction was stopped, the catalyst flushed with nitrogen and then regenerated using an oxygen flow of 33.3 cc/min at the same reaction temperature. The catalyst pretreatment can be with hydrogen, nitrogen or methane. The purpose of catalyst pretreatment is to reduce the catalyst and make it ready for reaction. Regeneration with oxygen is not limiting and can be carried out using air.

In Table A, X stands for conversion; S stands for selectivity; Y stands for yield in mol %; $iC_4$ stands for isobutane; and $iC_4=$ stands for isobutylene. The percent conversion obtained as shown in the below Tables represents the total isobutane converted to isobutylene and other products. The selectivity to isobutylene reported is the percent of isobutylene obtained based on isobutane converted, all percents being calculated on a molar basis. Productivity (Prod.$g_{HC}^=$/$g_{cat}$.h) is defined as grams of isobutylene ($g_{HC}^=$) produced per gram of catalyst, per hour. Feedstock consumption (Cons.$g_{HC}$/$g_{cat}$.h) is defined as grams of isobutane consumed per gram, per hour.

TABLE A

Effect of $O_2$, $CO_2$ and $CH_4$ Promoter Addition to Isobutane Dehydrogenation Reaction

| Ex. # | Promoter type | X, $iC_4$ | S, $iC_4=$ | Y, $iC_4=$ | Coke | H2 peak area | Prod.$g_{C4}=$/$g_{cat}$. h | Cons.$g_{C4}$/$g_{cat}$. h |
|---|---|---|---|---|---|---|---|---|
| 1 | None | 72.7 | 56.6 | 41.2 | 31.4 | 274 | 0.33 | 0.61 |
| 2 | $O_2$ | 69.4 | 67.0 | 46.5 | 27.4 | 276 | 0.36 | 0.56 |
| 3 | $CO_2$ | 68.2 | 69.3 | 47.2 | 25.0 | 228 | 0.37 | 0.55 |
| 4 | $CH_4$ | 73.4 | 53.5 | 39.3 | 35.7 | 282 | 0.31 | 0.60 |

As can be seen from these results, addition of $CO_2$ to the gas feed, as per Example 3, decreases isobutane conversion, increases isobutene selectivity, and lowers coke formation. In other words, catalyst productivity is increased and feed consumption is lowered; consequently process profitability can be enhanced at a very low additional cost. On the other hand, the addition of $CH_4$ results only in a negative impact on overall dehydrogenation performance, decreasing conversion and selectivity, and increasing coke production. As can further be determined from Table A, The use of $CO_2$ as opposed to $O_2$ results in a relative lowering of hydrogen formation by around 17%. However this is compensated for by the relative advantages of the use of a "friendly" gas promoter such as $CO_2$, and the correlative savings on costly explosion protection equipment.

In Examples 5–10, whose results are summarized below in Table B, the functional effect of $CO_2$ on isobutane dehydrogenation on a bigger scale is demonstrated. Using a fixed bed commercial catalyst, i.e., the catofin catalyst as described above, under atmospheric pressure, however in adiabatic conditions rather than isothermal conditions as was done in Examples 1–4, 15 gm of the catalyst were loaded into ¾ inch diameter reactor in its original extrudate shape. Reactor inlet temperature was set to 580 deg. C. Before reaction the catalyst was reduced at 580 deg. C. using 100 cc/min flow of H2/CH4 (50:50) for 3.15 minutes and reaction gas was then introduced at a feed loading of W/F=12. Analysis of reaction products were taken at in table specified times. Reported results represent catalyst activity measured after 5 minutes of reaction except for Examples 6 and 9 which were measured after 8 minutes of reaction.

As in Table A, in Table B X stands for conversion; S stands for selectivity; Y stands for yield in mol %; $iC_4$ stands for isobutane; and $iC_4=$ stands for isobutylene. The percent conversion obtained represents the total isobutane converted to isobutylene and other products. The selectivity to isobutylene reported is the percent of isobutylene obtained based on isobutane converted, all percentages being calculated on a molar basis. Productivity (Prod.$g_{HC}^=$/$g_{cat}$.h) is defined as grams of isobutylene ($g_{HC}^=$) produced per gram of catalyst, per hour. Feedstock consumption (Cons.$g_{HC}$/$g_{cat}$.h) is defined as grams of isobutane consumed per gram of catalyst, per hour.

TABLE B

Effect of CO2 Concentration on Isobutane Dehydrogenation

| Ex. # | CO2/iC4 | Reaction time, min | X, C4 | S, $iC_4=$ | Y, $iC_4=$ | S, Coke | Prod.$g_{C4}=$/$g_{cat}$. h | Cons.$g_{C4}$/$g_{cat}$. h |
|---|---|---|---|---|---|---|---|---|
| 5 | 0 | 5 | 50.4 | 75.9 | 38.2 | 19.3 | 0.31 | 0.42 |
| 6 | 0 | 8 | 44.0 | 77.6 | 34.1 | 8.4 | 0.27 | 0.37 |
| 7 | 0.0135 | 5 | 51.1 | 81.0 | 41.4 | 13.2 | 0.33 | 0.42 |
| 8 | 0.0274 | 5 | 48.6 | 80.1 | 38.9 | 7.5 | 0.31 | 0.39 |
| 9 | 0.0274 | 8 | 41.3 | 94.3 | 38.9 | 3.5 | 0.31 | 0.33 |
| 10 | 0.0417 | 5 | 48.3 | 72.4 | 35.0 | 24.3 | 0.27 | 0.39 |

These results show that the use of $CO_2$ as a promoter significantly improves the dehydrogenation reaction performance. Very limited amounts of $CO_2$ can lead to this enhancement. Coke formation has been dramatically lowered at a $CO_2$/isobutane ratio of 0.0274. Among the above examples, best results were obtained using a $CO_2$/isobutane ratio of 0.0274 as seen in Example 9. Here the selectivity was maximized, coke formation was minimized, and the feedstock consumption was the lowest. If overall yield (or productivity) is critical, and the process economics can justify higher coke formation and higher feedstock consumption, then a slightly lower $CO_2$/alkane ratio may be desired, as seen, for example, in Example 7.

Figure 1:
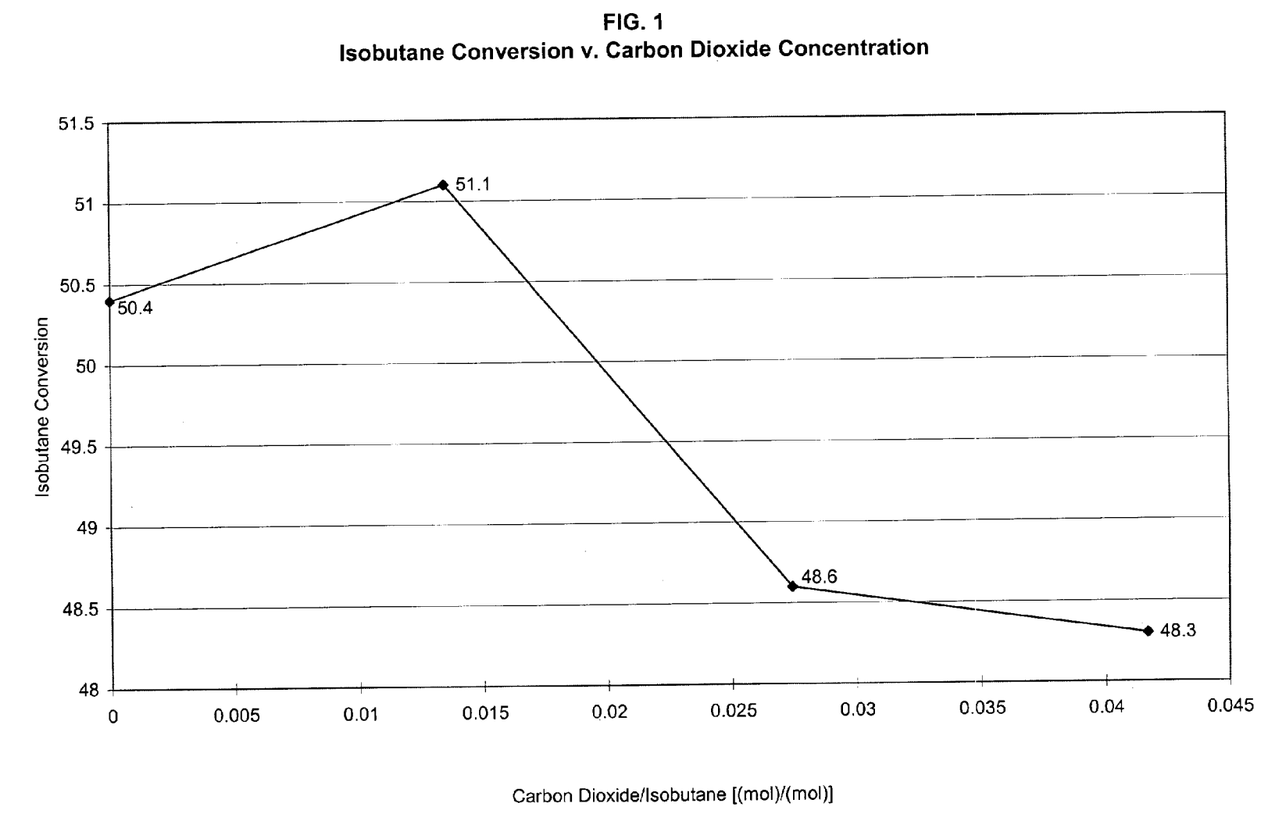
FIG. 1 is a graph depicting isobutane conversion as a function of carbon dioxide concentration for an exemplary data series using the process of the present invention.
Figure 2:
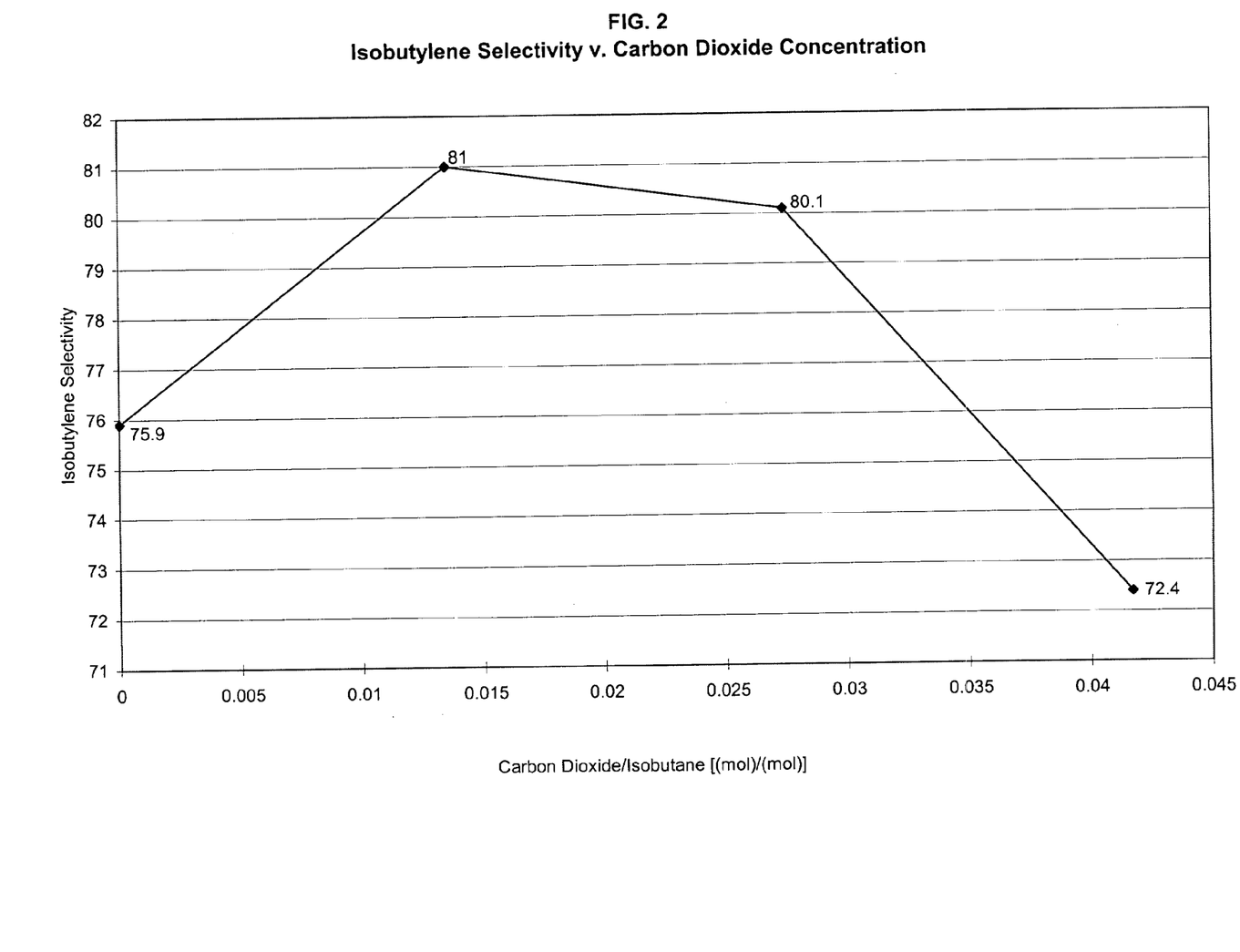
FIG. 2 is a graph depicting isobutylene selectivity as a function of carbon dioxide concentration for an exemplary data series using the process of the present invention.
Figure 3:
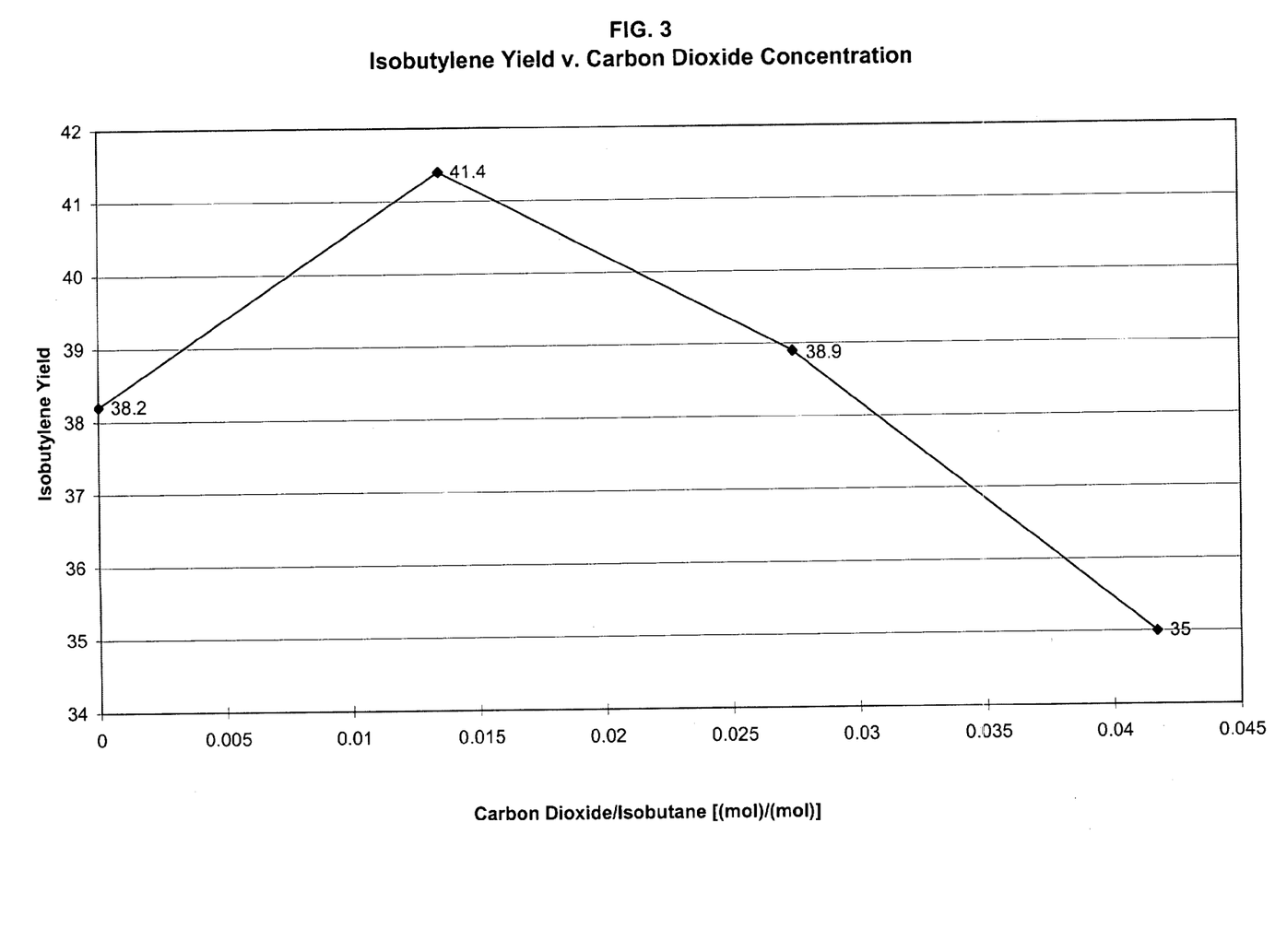
FIG. 3 is a graph depicting isobutylene yield as a function of carbon dioxide concentration for an exemplary data series using the process the present invention.
Figure 4:
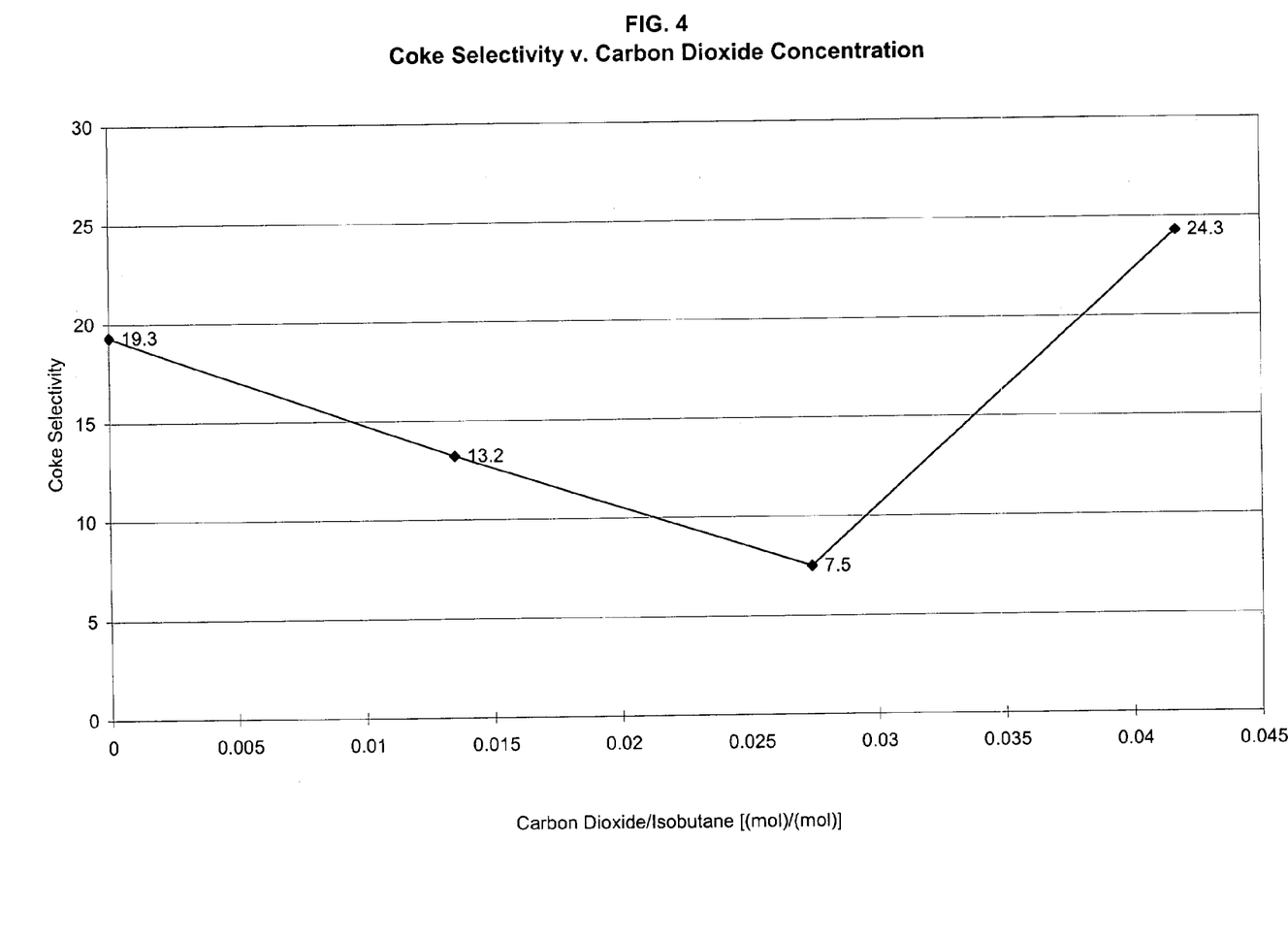
FIG. 4 is a graph depicting coke selectivity as a function of carbon dioxide concentration for two exemplary data series using the process of the present invention.

The results of Examples 5, 7, 8 and 10 were selected and graphed in FIGS. 1 through 4. From FIGS. 1, 2, and 3 it can be seen that isobutane conversion drops while isobutylene selectivity and yield increases as the ratio of carbon dioxide to isobutane in the feed increases to a maximum at a $CO_2$/isobutane molar ratio of 0.0135. A further increase in carbon dioxide concentration results in decreases in both conversion as well as selectivity. However, FIG. 4 indicates that coke selectivity and (from Table B) feedstock consumption continues to decrease until reaching a minimum at a $CO_2$/isobutane molar ratio of 0.0274. A higher or lower $CO_2$/isobutane molar ratio would likely result in higher coke selectivity.

Figure 5:
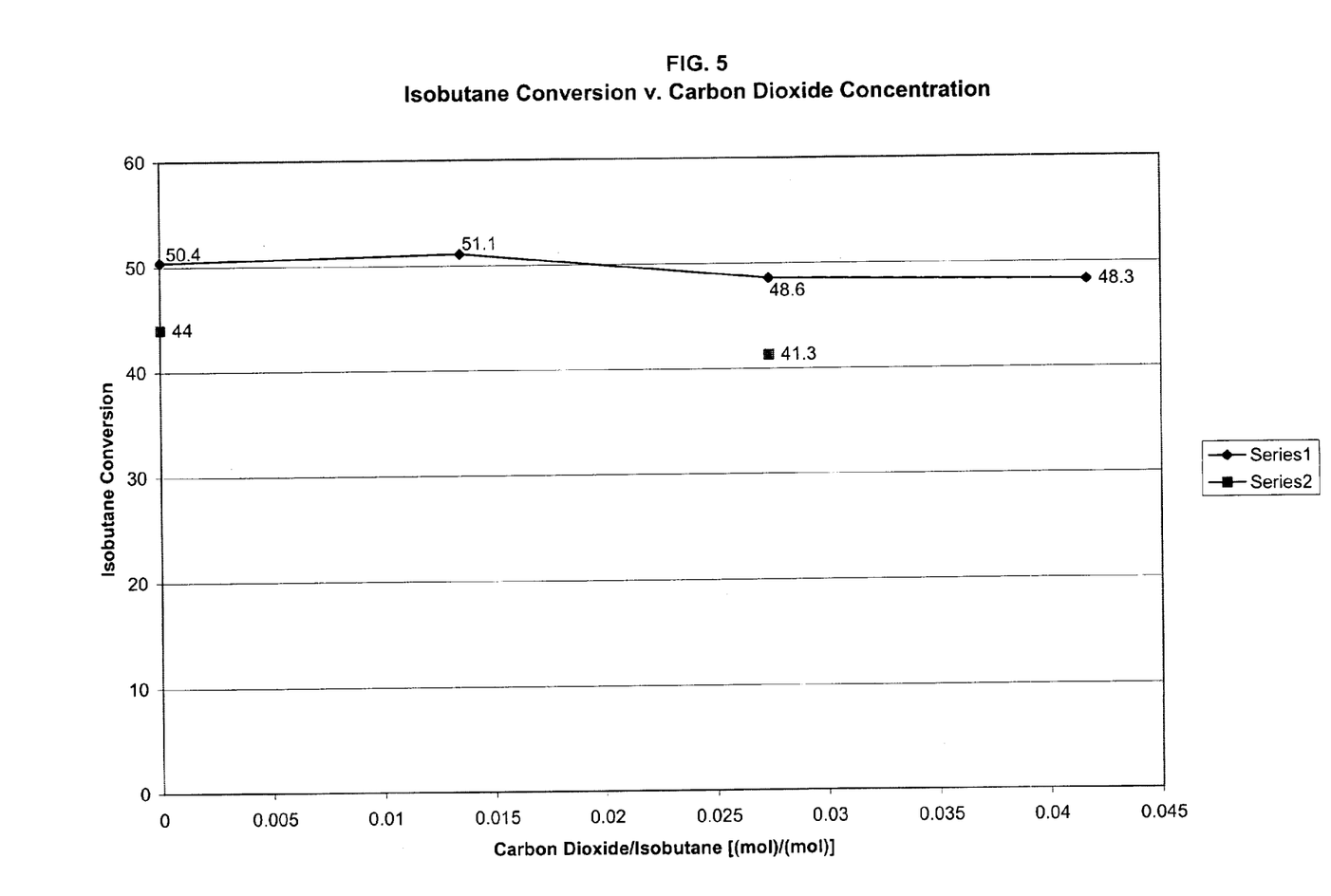
FIG. 5 is a graph depicting isobutane conversion as a function of carbon dioxide concentration for two exemplary data series using the process of the invention.
Figure 6:
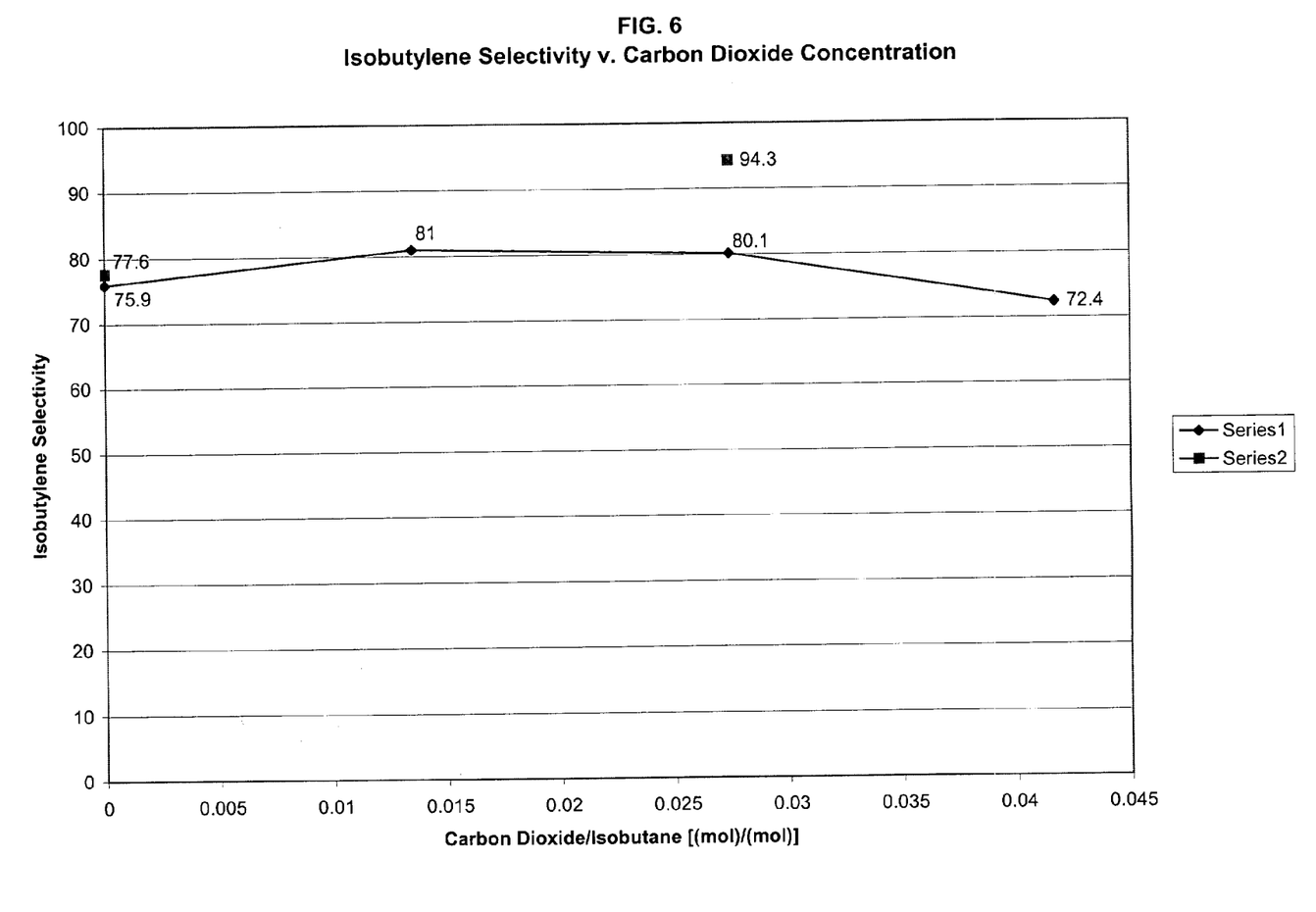
FIG. 6 is a graph depicting isobutylene selectivity as a function of carbon dioxide concentration for two exemplary data series using the process of the present invention.
Figure 7:
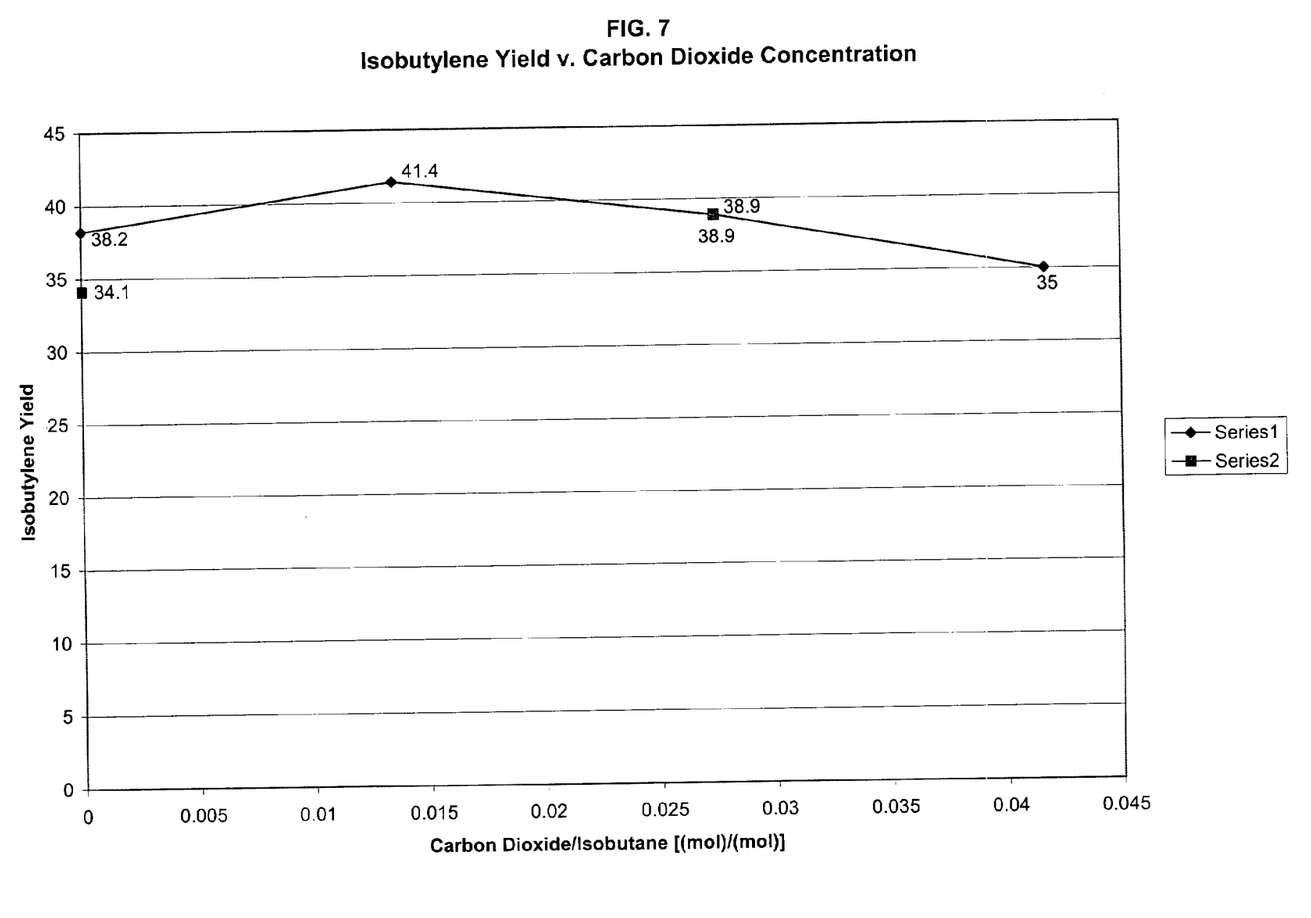
FIG. 7 is a graph depicting isobutylene yield as a function of carbon dioxide concentration for two exemplary data series using the process of the present invention.
Figure 8:
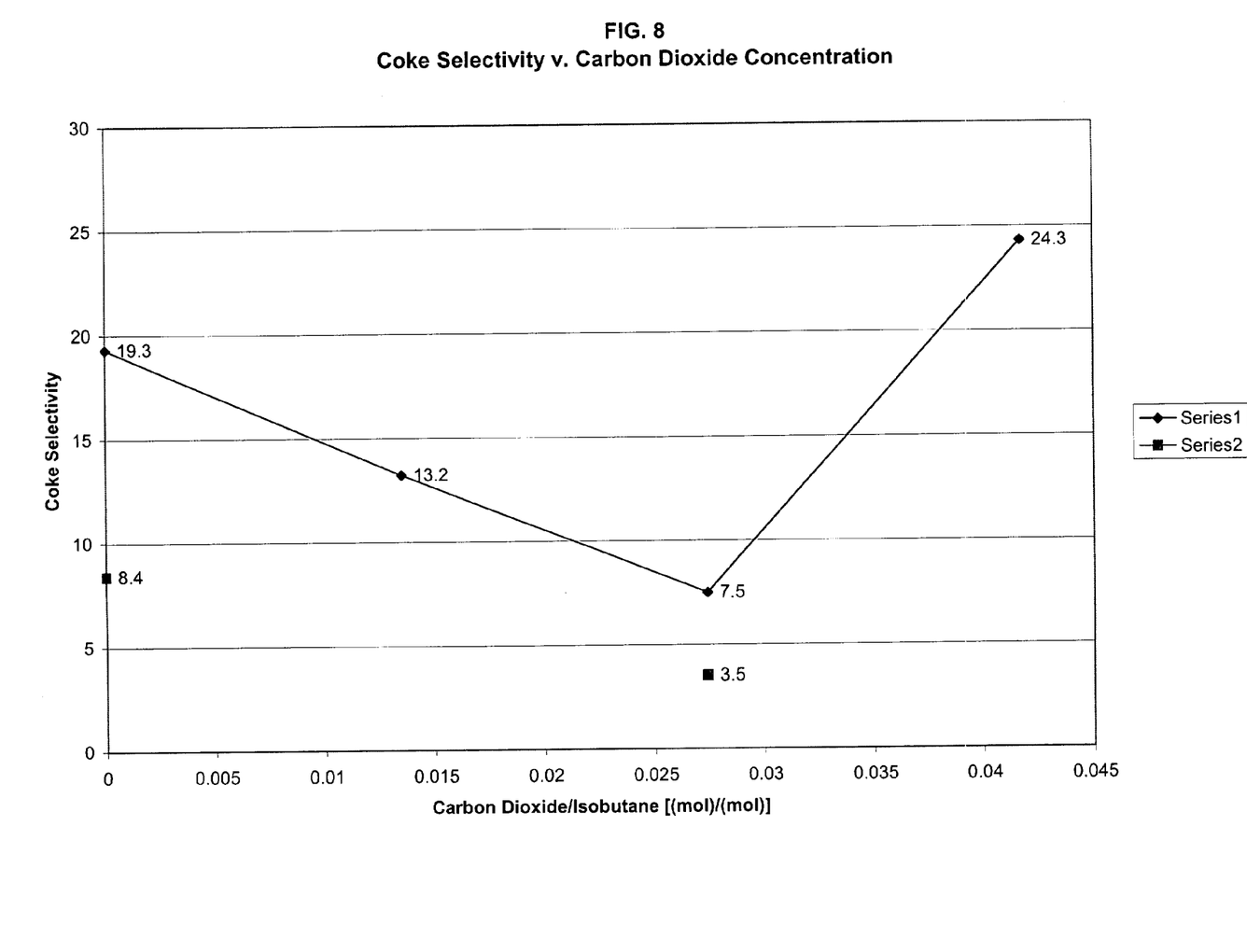
FIG. 8 is a graph depicting coke selectivity as a function of carbon dioxide concentration for two exemplary data series using the process of the present invention.

In addition, carbon dioxide addition according to the present invention enables continued isobutane savings and more isobutylene productivity at longer reaction times (Examples 6 and 9), and due to less coke formation, this allows an extended dehydrogenatin reaction time. FIGS. 5 through 8 depict the plots from FIGS. 1–4 superimposed with the data from Examples 6 and 9 (i.e., the examples where an eight minute reaction time was utilized), for comparison purposes. In FIGS. 5 through 8, the original plots from each of FIGS. 1 through 4 are respectively represented as the "Series 1" data, and the data from examples 6 and 9 is depicted as the "Series 2" data. The Series 1 data is connected by line segments, whereas the Series 2 data is not. From these plots, which superimpose the five and eight minute reaction results on the same independent variable range, the function of carbon dioxide as a selective controller of chromium redox properties is clearly demonstrated. It is shown that the oxidation of chromium by carbon dioxide molecules proceeds much faster than the oxidation of hydrogen or coke active species at the catalyst surface. Thus, within the range of $CO_2$ concentration depicted in the figures, values can be chosen to maximize selectivity for the desired olefin, or to maximize absolute productivity, as described above.

Having thus described in detail preferred embodiments of the present invention, it is to be understood that the invention defined by the appended claims is not limited to particular details set forth in this description as many variations thereof are possible without departing from the spirit or scope of the present invention.

What is claimed is:

1. A process for the dehydrogenation of isobutane comprising contacting isobutane with a chromium-based dehydrogenation catalyst which comprises 12% to 18% by weight chromium in the presence of carbon dioxide at a temperature of from about 400° C. to 700° C., a pressure of from about 0.1 to about 10 atmospheres, wherein the molar ratio of isobutane to carbon dioxide is about 1:0.0001 to 1:0.045.

2. The process of claim 1, wherein the temperature is from about 520° C. to about 700° C.

3. The process of claim 1, wherein the temperature is from about 540° C. to about 640° C.

4. The process of claim 1, wherein the isobutane dehydrogenation is performed over a fixed bed catalyst, a moving bed catalyst or a fluidized bed catalyst.

5. The process of claim 1, wherein said contacting is in the presence of an inert diluent.

6. The process of claim 5, wherein the inert diluent comprises methane, ethane, propane, nitrogen, or steam.

7. The process of claim 2, wherein said contacting is in the presence of methane, ethane, propane, nitrogen or steam.

8. The process of claim 3, wherein said contacting is in the presence of methane, ethane, propane, nitrogen or steam.

9. The process of claim 1, wherein the isobutane to carbon dioxide molar ratio is between about 1:0.0005 to 1:0.040.

10. The process of claim 1, wherein the isobutane to carbon dioxide molar ratio is between about 1:0.001 to 1:0.040.

11. The process of claim 1, wherein the isobutane to carbon dioxide molar ratio is between about 1:0.01 to 1:0.040.

12. The process of claim 1, wherein the amount of carbon dioxide present in relation to the amount of chromium in said catalyst is about 0.0001 to 0.001 gram mole of carbon dioxide per gram chromium in the catalyst.

13. The process of claim 2, wherein the amount of carbon dioxide present in relation to the amount of chromium in said catalyst is about 0.0002 and 0.0008 gram mole of carbon dioxide per gram chromium in the catalyst.

14. The process of claim 3, wherein the amount of carbon dioxide present in relation to the amount of chromium in said catalyst is about 0.0001 to 0.001 gram mole of carbon dioxide per gram chromium in the catalyst.

* * * * *